(12) United States Patent
Hiramatsu et al.

(10) Patent No.: US 7,824,036 B2
(45) Date of Patent: Nov. 2, 2010

(54) OPHTHALMIC ULTRASONIC MEASUREMENT APPARATUS, AND AN OPHTHALMIC MEASUREMENT METHOD

(75) Inventors: Hiroyuki Hiramatsu, Toyokawa (JP); Yukinobu Ban, Nishio (JP)

(73) Assignee: Nidek, Co., Ltd., Gamagori-shi (JP)

( * ) Notice: Subject to any disclaimer, the term of this patent is extended or adjusted under 35 U.S.C. 154(b) by 96 days.

(21) Appl. No.: 12/222,018

(22) Filed: Jul. 31, 2008

(65) Prior Publication Data

US 2009/0033869 A1    Feb. 5, 2009

(30) Foreign Application Priority Data

Aug. 3, 2007 (JP) .............................. 2007-203686

(51) Int. Cl.
*A61B 3/10* (2006.01)
(52) U.S. Cl. .................. 351/221; 351/205; 351/246
(58) Field of Classification Search .................. 351/221
See application file for complete search history.

(56) References Cited

U.S. PATENT DOCUMENTS 5,347,331 A * 9/1994 Isogai et al. .................. 396/18
5,912,721 A * 6/1999 Yamaguchi et al. ......... 351/210
6,312,393 B1* 11/2001 Abreu ........................ 600/558
2006/0025685 A1* 2/2006 dela Houssaye ............ 600/443
2008/0079898 A1 4/2008 Miwa et al.

FOREIGN PATENT DOCUMENTS

JP    A 2001-187022    7/2001
JP    A 2008-86527    4/2008

* cited by examiner

*Primary Examiner*—Jessica T Stultz
(74) *Attorney, Agent, or Firm*—Oliff & Berridge, PLC

(57) ABSTRACT

An ophthalmic ultrasonic measurement apparatus capable of narrowing differences in measurement results obtained by the apparatus which are made because of differences among examiners who operate the apparatus comprises an ultrasonic probe arranged to be brought into contact with a cornea of an examinee's eye, a calculation unit arranged to obtain a measured value of a length from the cornea to a given section inside the eye based on an echo from the eye by an ultrasonic wave which is emitted from the probe, and a memory arranged to store information on examiners and adjustment information for narrowing differences in measured values of the length which are made because of differences among the examiners while the adjustment information is associated with the examiners' information, wherein the calculation unit corrects the obtained measured value using the stored adjustment information.

1 Claim, 2 Drawing Sheets

FIG. 3

INFORMATION LIST

| EXAMINER NAME | ADJUST VALUE |
|---|---|
| AA BB | 0.10 |
| CC DD | -0.12 |
| EE FF | 0.34 |
| GG HH | 0.05 |
| II JJ | -0.09 |
| | |
| | |

[ENTRY]
[MODIFY]
[DELETE]

ENTRY OF INFORMATION

EXAMINER NAME [KK LL]
ADJUST VALUE [-0.07] mm
[OK] [CANCEL]

FIG. 4

EXAMINER IS [AA BB ▽]  (30)

ECHO WAVEFORM

PACHY

MEASURED VALUE [25.00] mm
ADJUST VALUE [0.10] mm
CORRECTED VALUE [25.10] mm

US 7,824,036 B2

OPHTHALMIC ULTRASONIC MEASUREMENT APPARATUS, AND AN OPHTHALMIC MEASUREMENT METHOD

BACKGROUND OF THE INVENTION

1. Field of the Invention

The present invention relates to an ophthalmic ultrasonic measurement apparatus which measures an axial length of an examinee's eye or the size of a given constituent part of the eye by bringing an ultrasonic probe into contact with a cornea of the eye, and an ophthalmic measurement method.

2. Description of Related Art

There is known an ophthalmic ultrasonic measurement apparatus which measures an axial length of an examinee's eye or the size of a given constituent part of the eye by bringing an ultrasonic probe into contact with a cornea of the eye. However, when measurement of an axial length of an examinee's eye or the size of a given constituent part inside the eye is performed using such an apparatus, there is a problem that differences could be made in results of the measurement because of differences among examiners who operate the apparatus. For example, a measured value of the axial length varies because the degree of a hollow in a cornea of an examinee's eye which is made when bringing the probe into contact with the cornea varies among the examiners. To be more specific, in the case of the examiner who tends to push the cornea relatively firmly with the probe, the degree of the hollow is larger, resulting in a smaller measured value of the axial length, while in the case of the examiner who tends to push the cornea relatively lightly with the probe, the degree of the hollow is smaller, resulting in a larger measured value of the axial length.

SUMMARY OF THE INVENTION

An object of the invention is to overcome the problem described above and to provide an ophthalmic ultrasonic measurement apparatus which is capable of narrowing differences in measurement results obtained by the apparatus which are made because of differences among examiners who operate the apparatus, and an ophthalmic measurement method.

To achieve the objects and in accordance with the purpose of the present invention, an ophthalmic ultrasonic measurement apparatus comprises an ultrasonic probe arranged to be brought into contact with a cornea of an examinee's eye, a calculation unit arranged to obtain a measured value of a length from the cornea to a given section inside the eye based on an echo from the eye by an ultrasonic wave which is emitted from the probe, and a memory arranged to store information on examiners and adjustment information for narrowing differences in measured values of the length which are made because of differences among the examiners while the adjustment information is associated with the examiners' information, wherein the calculation unit corrects the obtained measured value using the stored adjustment information.

In another aspect of the present invention, an ophthalmic measurement method for correcting a measured value of a length from a cornea of an examinee's eye to a given section inside the eye which is measured using an ultrasonic probe comprises the steps of storing information on examiners and adjustment information for narrowing differences in measured values of the length which are made because of differences among the examiners while the adjustment information is associated with the examiners' information, inputting a measured value of the length, and correcting the inputted measured value using the stored adjustment information.

Yet, in another aspect of the present invention, an ophthalmic measurement method for measuring a length from a cornea of an examinee's eye to a given section inside the eye by bringing an ultrasonic probe into contact with the cornea and correcting a measured value of the length comprises the steps of obtaining a measured value of the length from the cornea to the given section inside the eye based on an echo from the eye by an ultrasonic wave which is emitted from the probe, storing information on examiners and adjustment information for narrowing differences in measured values of the length which are made because of differences among the examiners while the adjustment information is associated with the examiners' information, and correcting the obtained measured value using the stored adjustment information.

Additional objects and advantages of the invention are set forth in the description which follows, are obvious from the description, or may be learned by practicing the invention. The objects and advantages of the invention may be realized and attained by the ophthalmic ultrasonic measurement apparatus and the ophthalmic measurement method in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

FIG. 3 is a view showing an example of a registration screen for registering examiners' information and adjustment information in the apparatus; and FIG. 4 is a view showing an example of a measurement screen.

DETAILED DESCRIPTION OF THE PREFERRED EMBODIMENTS

Figure 1:
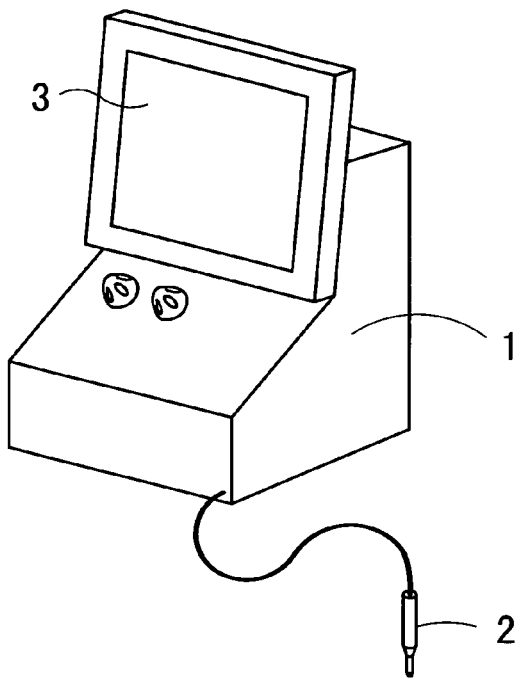
FIG. 1 is an external schematic view showing an ophthalmic ultrasonic measurement apparatus according to a preferred embodiment of the present invention.
Figure 2:
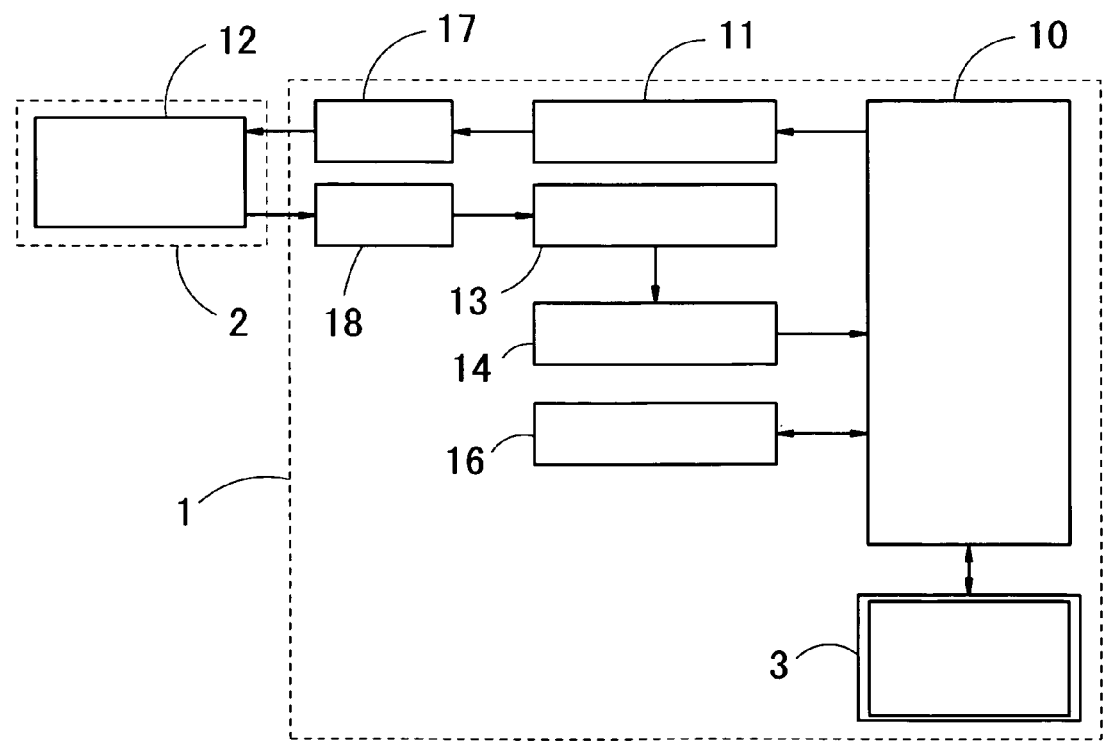
FIG. 2 is a schematic control block diagram of the ophthalmic ultrasonic measurement apparatus.

An ophthalmic ultrasonic measurement apparatus according to a preferred embodiment of the present invention which measures an axial length of an examinee's eye in A-mode (amplitude mode) is described below with reference to the accompanying drawings. FIG. 1 is an external schematic view showing the ultrasonic measurement apparatus according to the preferred embodiment of the present invention. FIG. 2 is a schematic control block diagram of the ultrasonic measurement apparatus.

A main body 1 of the apparatus is connected with an ultrasonic probe 2 for A-mode having a transducer 12. A color liquid crystal display panel 3 is provided on a front side of the main body 1. The display panel 3 has a touch panel function, and is arranged such that various measurement conditions can be set on a screen of the display panel 3.

A calculation and control unit 10 is included in the main body 1 and is arranged to control various circuits and constituent elements. The calculation and control unit 10 controls a clock generation circuit 11 to emit an ultrasonic wave from the transducer 12 via a transmitter 17. When a tip of the probe 2 is brought into contact with a cornea of the eye, echoes from sections (tissues) of the eye are received by the transducer 12 and are converted into digital signals by an A/D converter 13 via an amplifier 18. The calculation and control unit 10 samples data of the echoes converted into the digital signals and stores it in a memory 14, and based on the sampled echo data, calculates the length from the cornea (a corneal surface) to a retina of the eye, whereby a measured value of the axial length of the eye is obtained. The obtained measured value is stored in a memory 16 while displayed on the screen of the display panel 3.

In the memory 16, a program for obtaining the measured value of the axial length and correcting the obtained measured value is stored. In addition, in the memory 16, adjustment information for eliminating (or narrowing) differences in measured values of the axial length is stored associated with information on examiners. To be more specific, identification information such as a name and an ID number is stored for each of the examiners (no less than two examiners), and the adjustment information is stored associated with the examiners' information for each of the examiners.

FIG. 3 is a view showing an example of a registration screen for registering the examiners' information and the adjustment information in the apparatus. Screen display of the display panel 3 is arranged to be controlled by the calculation and control unit 10. Adjustment values are the adjustment information in the present preferred embodiment of the present invention, and the adjustment values are for eliminating (or narrowing) the differences in the measured values which are made because of differences among the examiners. The examiners whose adjustment values are capable of being set (registered) are those examiners by whom a state of pushing (a pushing force and other conditions) of the probe 2 to the cornea is made stable to some extent at the time of the measurement (i.e., those examiners whose pushing force and other conditions are stable so that the degree of a hollow in the cornea which is made when bringing the probe 2 into contact with the cornea becomes almost the same every time the contact is made).

Hereinafter, a description of a method for obtaining and registering the adjustment value for each of the examiners will be provided. First, an almost exact axial length of an eye of one examinee is obtained as a reference value of an axial length of the examinee's eye. In this case, measurement of the axial length is performed with a stable pushing force exerted to a cornea of the eye by a skilled examiner while, for example, the probe 2 is rested on a given probe stand.

Next, measurement of the axial length is performed with a varying pushing force of the probe 2 exerted to the cornea of the examinee's eye whose reference value of the axial length has been obtained, and measured values of the axial length which correspond to the plurality of various pushing forces are obtained. In this case, the probe 2 equipped with a pressure sensor for detecting the pushing force of the probe 2 to the cornea is used, and the measured values of the axial length are obtained while the pushing force is varied. Then, the plurality of obtained various measured values are compared with the reference value, and correlations between the pushing forces corresponding to the measured values and deviations of the measured values from the reference value are each obtained every time the measurement is performed (every time the pushing force is varied). This operation may be performed by one examiner alone, or may be performed by a plurality of examiners. In addition, this operation may be performed on one eye of an examinee, or may be performed on a plurality of eyes of examinees (reference values of axial lengths of all of the examinees need to be obtained).

After the correlations between the pushing forces of the probe 2 to the cornea, which are to exert influences upon the degree of a hollow in the cornea, and the variations in the measured value of the axial length are obtained in the above-described manner, the adjustment value for each of the examiners is obtained using the correlations. For example, in obtaining an adjustment value for one examiner, measurement is first performed by the examiner on a model eye (or a human eye) using the probe 2 in the usual manner, and a pushing force of the probe 2 at the time of the measurement is detected by the pressure sensor. Next, a deviation corresponding to the detected pushing force is obtained from the previously obtained correlations between the pushing forces and the variations in the measured value. The deviation thus obtained is to be used as the adjustment value for the examiner. In this manner, the adjustment value is obtained for each of the examiners.

Alternatively, it is also preferable that measured values of the axial length corresponding to a plurality of various pushing forces are obtained, which are used as a plurality of various reference values of the axial length while correlations between the reference values and the pushing forces corresponding to the reference values are each obtained every time the measurement is performed (every time the pushing force is varied), and the reference value corresponding to a detected pushing force of one examiner is obtained from the correlations, and the obtained reference value is used as the adjustment value for the examiner.

The operation of the apparatus having the above-described structure will be described. An examiner operates given switches on the screen of the display panel 3 and a measurement screen is displayed thereon (see FIG. 4), and then the examiner operates a pull-down button 30 and an information list prestored in the memory 16 is displayed thereon (see FIG. 3). Then, the examiner chooses his/her name. By this choice, information on the examiner is determined among the examiners' information stored in the memory 16, and an adjustment value corresponding to the examiner's information is read therefrom.

After the readout of the adjustment value, the probe 2 is brought into contact with a cornea of an examinee's eye and measurement is performed. When the probe 2 is brought into contact with the cornea, echoes from sections (tissues) of the eye are received by the transducer 12 and an echo waveform is displayed on the screen of the display panel 3 (see FIG. 4). The examiner adjusts the position, the angle or the like of the probe 2 so as to obtain an appropriate echo waveform while observing the echo waveform always displayed on the screen. Once an appropriate echo waveform is obtained, the examiner presses a given measurement starting switch.

Upon receipt of a trigger signal from the measurement starting switch, the calculation and control unit 10 samples data of the echoes which are received at that time. When the sampled echo data is appropriate, the calculation and control unit 10 calculates a measured value of an axial length of the eye, and stores the measured value in the memory 16.

Next, the calculation and control unit 10 corrects the measured value of the axial length stored in the memory 16 by using the adjustment value which is read therefrom, and obtains a corrected value of the axial length. For example, when the measured value is 25.00 mm and the adjustment value is 0.10 mm, a corrected value of 25.10 mm is obtained (25.00+0.10=25.10). The measured value, the adjustment value and the corrected value are displayed on the screen of the display panel 3.

Thus, the differences in the measurement results which are made because of the differences among the examiners who operate the probe 2 are narrowed. Besides, in a case where there is no need to correct the obtained measured value, or in a case where an examiner whose information is not registered is to perform measurement, correction of the measured value using an adjustment value is not performed.

In the descriptions above, it is arranged that choosing the examiner's information (i.e., inputting the selection signal of the examiner's information) allows the adjustment information (the adjustment value) corresponding to the examiner to be obtained; however, it is not limited thereto. For example, it may be arranged that a number of the adjustment value is directly set (inputted), or that the adjustment value is set (inputted) through operation of a given spinning button or a given pull-down button displayed on the screen of the display panel 3 (see FIG. 3 and FIG. 4).

In the descriptions above, the case of measuring an axial length of an examinee's eye is explained; however, it is not limited thereto. The present invention may be applied to any apparatus if the apparatus is capable of measuring the length from a cornea of an examinee's eye to a given section inside the eye (e.g., the depth of an anterior chamber of the eye) by bringing an ultrasonic probe into contact with the cornea.

In the descriptions above, the measurement, the correction processing and other operations in the ultrasonic measurement apparatus are explained; however, they are not limited thereto. For example, it may be arranged that the program according to the present invention, the examiners' information, the adjustment information and other information are stored on a hard disk or in a memory of a computer which does not include an ultrasonic probe, in which a measured value such as an axial length of an examinee's eye which is obtained by an external apparatus is inputted, and the above-described correction processing is thereby performed by a CPU. In this case, the input of the measured value may be made using an input unit such as a keyboard, a mouse and an input port of the computer, or may be made by wired or wireless transmission from an ophthalmic ultrasonic measurement apparatus. Besides, the above-described measurement program may be a portion of a program for determining the degree of an intraocular lens using measurement results obtained by an ophthalmic ultrasonic measurement apparatus.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic ultrasonic measurement apparatus comprising:
    an ultrasonic probe arranged to be brought into contact with a cornea of an examinee's eye;
    input means arranged to input examiner information on a plurality of examiners and measurement adjustment information that is associated with the examiner information;
    selecting means arranged to select one examiner of the plurality of examiners; and
    a calculation unit arranged to (1) obtain a measured distance between given tissues of the examinee's eye based on an echo signal that is reflected at the eye and received by the probe, (2) retrieve the measurement adjustment information based on the examiner information associated with the selected examiner, and (3) correct the obtained measured distance by applying the retrieved measurement adjustment information.

* * * * *